United States Patent [19]
Kiyomine et al.

[11] Patent Number: 5,612,023
[45] Date of Patent: Mar. 18, 1997

[54] COMPOSITION FOR PERMANENT WAVING OF HUMAN HAIR

[75] Inventors: Akira Kiyomine, Kawachi-gun; Yoshinori Nishizawa, Utsunomiya, both of Japan; Bernd Nöcker, Ober-Ramstadt; Burkhard Rose, Darmstadt, both of Germany

[73] Assignee: KAO Corporation, Japan

[21] Appl. No.: 633,953

[22] Filed: Apr. 15, 1996

[30]     Foreign Application Priority Data

Apr. 22, 1995  [DE]  Germany ................. 195 14 935.1

[51] Int. Cl.⁶ ................................................ A61K 7/09
[52] U.S. Cl. ............................ 424/70.5; 424/70.2
[58] Field of Search ........................... 424/401, 70.2, 424/70.5

[56]     References Cited

U.S. PATENT DOCUMENTS 5,068,102  11/1991  Tennigkeit et al. ............... 424/70.2
5,378,454  1/1995  Burmeister ........................ 424/70.5

FOREIGN PATENT DOCUMENTS

29506849-U1  8/1996  Germany.

*Primary Examiner*—John C. Bleutoe
*Assistant Examiner*—Robert H. Harrison
*Attorney, Agent, or Firm*—Dvorak and Traub

[57]     ABSTRACT

A permanent waving composition for human hair without any skin sensitizing effect comprises as reducing agent 1,3-propanediol monothioglycollate and 1,3-propanediol dithioglycollate alone or in admixture with other reducing agents, wherein the content of 1,3-propanediol dithioglycollate is not more than 10%, preferably less than 5% by wt., calculated to the monoester.

6 Claims, No Drawings

COMPOSITION FOR PERMANENT WAVING OF HUMAN HAIR

This invention comprises a composition for waving of human hair, i.e. a permanent waving composition, providing an excellent waving effect without damaging the hair and having a minimal skin sensitizing potential even after repeated application.

It is known that permanent waving is performed in two steps, i.e., the reductive splitting of the cystine disulfide bonds of the hair by the action of a reducing agent and the subsequent neutralization or fixation by the application of an oxidizing agent, thus restoring the cystine disulfide bonds. The reducing agent most frequently used today is thioglycolic acid, particularly as ammonium salt, although numerous other thio compounds have been proposed for this purpose, however, without practical success.

The thioglycollate compositions are normally used at a pH-value between 8 and 10, particularly from 8.5 to 9.5, which may lead to hair damage when the waving operation is repeated in short intervals.

It has been tried to overcome these disadvantages by the formulation of so-called "acidic permanent waving compositions" which are applied at a pH-value of about 6.8 to 7.8, i.e. almost neutral. The reducing agent most frequently used in these compositions is thioglycolic acid monoglycerol ester. However, this substance may have a sensitizing effect on some users, so that this solution is not optimal.

It has now been found that these problems may be overcome by the use of a composition comprising as reducing agent 1,3-propanediol monothioglycollate containing a low amount of 1,3-propanediol dithioglycollate alone or in admixture with other reducing agents; this preparation provides permanent waving compositions which act at a pH-value where no hair damage happens but which achieve a good waving effect German Patent Application No.22 55 800 already discloses permanent waving compositions comprising esters from polyvalent alcohols and lower mercapto carboxylic acids as active agents, i.e. reducing agents. Among others, 1,2-propyleneglycol monothioglycolic acid ester is mentioned. PCT-Patent WO-A 93/01791 follows this course describing an azeo-tropic mixture of two isomers of 1,2-propanediol monothio-glycollate and their use as reducing agents in permanent waving compositions.

However, the state of the art does not suggest any such use for 1,3-propanediol monothioglycollate.

From the aspect of its hair waving properties, 1,3-propanediol monothioglycollate (PMTG), used as reducing agent according to the invention, contains not more than 10% by wt., particularly less than 5% by wt., calculated to the PMTG, of 1,3-propanediol dithioglycollate.

Optimum waving results are achieved if the diester content is not more than 1% by wt.

The production of 1,3-PMTG is performed by direct esterification of 1,3-propanediol with thioglycolic acid at about 150° to 200° C.

After removing the remaining original products by distillation, 1,3-propanediol monothioglycollate with about 1% by wt. 1,3-propanediol dithioglycollate is obtained at a boiling point from 89° to 91° C. at 0.2 mmHg.

The solubility of 1,3-GMTG in water is more than 25% by wt., which is advantageous for its use in permanent waving compositions.

The preferred proportion of 1,3-GMTG in the permanent waving compositions according to the invention is between 5% and 25% by wt., calculated to the total composition of the reducing compound phase (i.e., excluding fixing or neutralizing agents), particularly between about 10% and about 20% by wt.

If further reducing agents are included in admixture with 1,3-GMTG in the permanent waving compositions according to the invention, their proportion is preferably below 50%, calculated to the total quantity of reducing agents.

Such additional reducing agents are, e.g., thioglycolic acid, thiolactic acid and the salts thereof, other esters of thioglycolic acid and thiolactic acid such as 1,2-propanediol monothioglycollate or thiolactate, thioamino acids and their derivatives, e.g., cysteine and the salts thereof, N-acetyl cysteine, thioglyceryl ether of the structure disclosed in German Patent Application No.42 09 327, etc.

In any case, however, 1,3-PMTG is the main component of the total reducing agent, preferably about 65% to 100% thereof.

If 1,3-PMTG is used in admixture with other reducing agents, its proportion of the total reducing agent composition must obviously be reduced accordingly; the amount depends on the type and quantity of the other reducing agent(s).

The total reducing agent percentage is usually 2.5% to about 15% by wt., calculated to free thioglycolic acid as a reference substance.

If necessary, the reducing permanent waving compositions may also contain a quantity of alkalizing agents. Their amount depends on the reducing agent and the pH-value selected for the composition. Preferably, the reducing agent composition comprises about 0.1% to about 5%, particularly 0.5% to about 2.5% by wt. thereof.

Preferred alkalizing agents within the scope of the invention are ammonium carbamate, ammonia and (or) ammonium (bi)-carbonate. The desired pH-value is adjusted in the range between about 6.5 and about 8.5, preferably from 7 to 8.

The permanent waving compositions used according to the invention preferably also contain surfactants. Their proportion is about 0.1% to about 10%, particularly between about 1% and about 5% by wt. of the reducing agent composition.

The surfactants used in both reducing agent compositions and neutralizing compositions are preferably the known anionic materials which are optionally also used in combination with nonionic surfactants.

Suitable anionic surfactants are particularly the known alkyl ether sulfates and carboxylic acids, preferably in the form of their alkali salts, and protein fatty acid condensates. Suitable nonionic surfactants are particularly $C_8$–$C_{18}$-fatty alcohol polyglycol ethers, fatty acid polyglycol esters, fatty acid alkanolamides, amine oxides and, preferably, $C_8$–$C_{18}$-alkyl polyglycosides.

It is also possible to use amphoteric surfactants, such as the known betaines and amido betaines and, particularly in cationic neutralizers, cationic surfactants such as quaternary ammonium compounds.

Other desirable components of the reducing agent compositions according to the invention are $C_3$–$C_6$-alkanediols or the ethers thereof, particularly mono-$C_1$–$C_3$-alkyl ethers.

Preferred substances in this context are 1,2- and 1,3-propane-diol, 1-methoxypropanol(-2), 1-ethoxypropanol(-2), 1,3- and 1,4-butanediol, diethyleneglycol and the monomethyl and monoethyl ethers thereof as well as dipropyleneglycol and the monomethyl and monoethyl ether thereof.

The preferred proportion of these diols is in the range from 0.5% to 30%, more preferably about 1% to about 15%, particularly about 5% to about 10% by wt. of the reducing agent composition.

In addition to the $C_3$–$C_6$-alkanediols or the ethers thereof, propylenecarboxylate (4-methyl-1,3-dioxolane-2-one), N-alkyl pyrrolidone, glycerol and urea may also be used.

The compositions used according to the invention may naturally also comprise any materials usually employed in permanent waving compositions; they may be present as (aqueous) solutions, emulsions, creams, foams, etc.

To avoid repetition, reference is rather made to the state of the art, as described in, e.g., "Ullmann's Encyclopedia of Industrial Chemistry", Vol. A12 (1986), pp. 588 to 591 and particularly in the monography of K. Schrader "Grundlagen und Rezepturen der Kosmetika", 2nd Ed. (1989, Hüthig Verlag, Heidelberg), pp. 823 to 840, as well as in the survey by D. Hollenberg et al. in "Seifen-Öle-Fette-Wachse", 117 (1991), pp. 81 to 87.

The compositions and individual ingredients disclosed there, to which reference is expressly made, may also be used in the compositions of the present invention.

If desired, also a preconditioning treatment preparation may be applied before the application of the reducing agent composition, as described, e.g., in German Patent Application No. 37 40 926. Upon application of this preconditioning treatment, the hair is wound on curlers, whereafter the reducing agent composition is applied. After about 15 to 30 minutes processing time and rinsing with water, the hair is neutralized by the application of the usual peroxide or bromate compositions sufficiently known in the art.

In addition, an intermediate treatment may be provided between the reducing step and the neutralizing step.

The following examples illustrate the invention in detail.

EXAMPLE 1

| Permanent wave for normal hair | |
| --- | --- |
| 1,3-Propanediol monothioglycollate, (<1% 1,3-propanediol dithiodiglycollate) | 17.5 (% by wt.) |
| Ammonium bicarbonate | 0.9 |
| Cationic polymer | 0.5 |
| C$_9$—C$_{11}$-alkyl polyglucoside (P.G. ≈ 1.3) | 1.0 |
| Solubilizer (castor oil polyglycol fatty acid ester) | 0.5 |
| Perfume oil | 0.4 |
| Water | @ 100.0 |
| Adjusted with NH$_3$ to | pH 7.0. |

This permanent waving solution was applied onto wound hair and, after 20 minutes processing time, rinsed with water, whereupon the hair was neutralized as usual with the following hydrogen peroxide composition:

| Hydrogen peroxide | 1.00 (% by wt.) |
| --- | --- |
| Sodium lauryl diglycol ethersulfate | 2.50 |
| Phenacetin | 0.02 |
| Water | @ 100.00 |
| Adjusted with H$_3$PO$_4$ to | pH 3.5. |

An expressive and long-lasting permanent waving without any skin sensitization was achieved.

EXAMPLE 2

| Permanent wave for normal hair | |
| --- | --- |
| 1,3-Propanediol monothioglycollate (<2.5% 1,3-propanediol dithioglycollate) | 17.50 (% by wt.) |
| Ammonium carbamate | 0.75 |
| Chlorophyllin | 0.05 |
| Protein hydrolyzate | 0.30 |
| Coconut amidopropyl betaine | 1.00 |
| Solubilizer (Castor oil polyglycol fatty acid ester) | 0.50 |
| Perfume oil | 0.40 |
| Water | @ 100.00 |
| Adjusted with NH$_3$ to | pH 7.2. |

The waving procedure was carried out according to Example 1, but due to the presence of chlorophyllin (cf. European Patent No. 515 768), the waving result was even better than that obtained with the composition of Example 1.

EXAMPLE 3

| Permanent wave for porous hair | |
| --- | --- |
| 1,3-Propanediol monothioglycollate (<5% 1,3-propanediol dithioglycollate) | 14.5 (% by wt.) |
| Ammonium hydrogencarbonate | 0.5 |
| 1,2-Propanediol | 6.0 |
| Laureth-23 | 1.0 |
| Perfume oil | 0.5 |
| Water | @ 100.0 |
| Adjusted with ammonia to | pH 6.6. |

If this formulation is applied to porous hair, a permanent wave is achieved having similar properties as obtained with the composition according to Example 1.

Example 4

| Universally applicable permanent wave | |
| --- | --- |
| 1,3-Propanediol monothioglycollate (<1% 1,3-propanediol dithioglycollate) | 18.0 (% by wt.) |
| Ammonium thioglycollate | 1.0 |
| Diammonium dithiodiglycollate | 2.0 |
| Nonoxynol-20 | 1.0 |
| Perfume oil | 0.4 |
| Water | @ 100.0 |
| Adjusted with NH$_3$ to | pH 8.0. |

With this composition an excellent waving result is achieved without any sensitization of both client and hairdresser.

We claim:

1. Composition for permanent waving of human hair, comprising as reducing agent 1,3-propanediol monothioglycollate and 1,3-propanediol dithioglycollate in a proportion related to propanediol monothioglycollate of not more than 10% by wt. alone or in admixture with other reducing agents.

2. Composition according to claim 1, wherein the proportion of 1,3-propanediol dithioglycollate, calculated to 1,3-propanediol monothioglycollate, is not more than 5% by wt.

3. Composition according to claim 2, wherein the proportion of 1,3-propanediol dithioglycollate, calculated to 1,3-propanediol monothioglycollate, is not more than 1% by wt.

4. Composition according to claim 1, wherein the proportion of 1,3-propanediol monothioglycollate is 5% to 25% by wt., calculated to the total composition.

5. Composition according to claim 1, wherein the composition comprises 0.5% to 15% by wt., calculated to the total composition, of at least one polyalcohol or a methyl or ethyl ether thereof.

6. Composition according to claim 1, wherein its pH-value is less than 8.5.

* * * * *